(12) United States Patent
Sadowski et al.

(10) Patent No.: US 6,428,528 B2
(45) Date of Patent: *Aug. 6, 2002

(54) NEEDLE ASSISTED JET INJECTOR

(75) Inventors: Peter L. Sadowski, Woodbury; David M. DeBoer, Waconia; Claude L. Berman, St. Paul; Paul R. Lesch, Jr., Lexington, all of MN (US)

(73) Assignee: Antares Pharma, Inc., Minneapolis, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/256,310

(22) Filed: Feb. 24, 1999

Related U.S. Application Data

(60) Provisional application No. 60/096,464, filed on Aug. 11, 1998.

(51) Int. Cl.[7] .............................................. A61M 31/00
(52) U.S. Cl. ........................ 604/511; 604/136; 604/157; 604/201; 604/239
(58) Field of Search .................................. 604/134–136, 604/138, 139, 156, 157, 182, 200, 202, 240, 244, 500, 511, 239

(56) References Cited

U.S. PATENT DOCUMENTS

| | | | |
|---|---|---|---|
| 3,605,744 A | 9/1971 | Dwyer | |
| 3,702,609 A | 11/1972 | Steiner | |
| 3,797,489 A | 3/1974 | Sarnoff | |
| 3,797,491 A | 3/1974 | Hurschman | |
| 3,892,237 A | 7/1975 | Steiner | |
| 4,127,118 A | 11/1978 | Latorre | |
| 4,227,528 A | 10/1980 | Wardlaw | |
| 4,258,713 A | 3/1981 | Wardlaw | |
| 4,282,986 A | 8/1981 | af Ekenstam et al. | |
| 4,378,015 A | 3/1983 | Wardlaw | |
| 4,553,962 A | 11/1985 | Brunet | |
| 4,634,027 A | * 1/1987 | Kanarvogel | |
| 4,719,825 A | 1/1988 | LaHaye et al. | |
| 4,790,824 A | 12/1988 | Morrow et al. | |
| 5,062,830 A | 11/1991 | Dunlap | |
| 5,080,648 A | 1/1992 | D'Antonio | 604/72 |
| 5,304,128 A | 4/1994 | Haber et al. | 604/68 |
| 5,318,522 A | 6/1994 | D'Antonio | 604/72 |
| 5,391,151 A | * 2/1995 | Wilmot | 604/139 |
| 5,505,694 A | 4/1996 | Hubbard et al. | |
| 5,569,190 A | 10/1996 | D'Antonio | 604/72 |
| 5,599,302 A | 2/1997 | Lilley et al. | |
| 5,637,094 A | * 6/1997 | Stewart, Jr. et al. | 604/135 |
| 5,769,138 A | 6/1998 | Sadowski et al. | |
| 5,951,528 A | * 9/1999 | Parkin | |
| 6,056,716 A | 5/2000 | D'Antonio et al. | 604/68 |
| 6,231,540 B1 | * 5/2001 | Smedegaard | 604/68 |

FOREIGN PATENT DOCUMENTS

| | | |
|---|---|---|
| WO | WO 92/19296 | 11/1992 |
| WO | WO 95/29720 | 11/1995 |
| WO | WO 97/14455 | 4/1997 |
| WO | WO 97/21457 | 6/1997 |
| WO | WO 97/48430 | 12/1997 |
| WO | WO 99/03521 | 1/1999 |
| WO | WO 99/22790 | 5/1999 |

* cited by examiner

*Primary Examiner*—Angela D. Sykes
*Assistant Examiner*—Jeremy Thissell
(74) *Attorney, Agent, or Firm*—Winston & Strawn

(57) ABSTRACT

A needle assisted jet injector and method for jet injecting medicament are disclosed. In one embodiment of the injector, the needle is retractably located within an injector nozzle assembly. Upon activation of the energy source, a portion of the needle extends past the nozzle assembly and penetrates the outer layer of skin to deliver the medicament via jet injection to a deeper region. After activation, the needle retracts back into the nozzle assembly. In another embodiment, the needle is fixed to the end of the nozzle assembly. In both embodiments, the length of the portion of the needle that penetrates the skin is less than 5 mm.

6 Claims, 12 Drawing Sheets

NEEDLE ASSISTED JET INJECTOR

This application claims the benefit of provisional application 60/096,464 filed Aug. 11, 1998.

FIELD OF THE INVENTION

The present invention is directed to a device for delivery of medicament, and in particular to a jet injector with a short needle to reduce the pressure at which the jet injector must eject the medicament for proper delivery.

BACKGROUND OF THE INVENTION

A wide variety of needleless injectors are known in the art. Examples of such injectors include those described in U.S. Pat. No. 5,599,302 issued to Lilley et al., U.S. Pat. No. 5,062,830 to Dunlap, and U.S. Pat. No. 4,790,824 to Morrow et al. In general, these and similar injectors administer medication as a fine, high velocity jet delivered under sufficient pressure to enable the jet to pass through the skin.

As the skin is a tissue composed of several layers and the injector is applied to the external surface of the outermost layer, the delivery pressure must be high enough to penetrate all layers of the skin. The layers of skin include, the epidermis, the outermost layer of skin, the dermis, and the subcutaneous region. The required delivery pressure is typically greater than approximately 4000 p.s.i. (measured as the force of the fluid stream divided by the cross-sectional area of the fluid stream).

Although this pressure is readily achievable with most injectors, there are some circumstances in which delivery of medicament to the subcutaneous region under a reduced pressure is desirable. For example, drugs that require a specific molecular structural arrangement, such as a linear protein configuration, may be rendered ineffective due to shear forces caused by the delivery of the drug at high pressures that alter the structural arrangement of the drug. As it is more difficult to deliver a large volume of fluid at a high pressure compared to a small volume, using a lower pressure facilitates delivery of a larger volume of fluid. Furthermore, the lower pressure could make manufacturing an injector device less expensive. The lower pressure would also reduce adverse stresses on the device and result in a corresponding increased useable device lifetime.

One of the advantages associated with jet injectors is the absence of a hypodermic needle. Given the aversion to needles possessed by some, the absence of a needle provides a psychological benefit. Even devices that utilize conventional hypodermic needles have attempted to capitalize on this psychological benefit. For example, self-injectors or auto-injectors like the ones disclosed in U.S. Pat. Nos. 4,553,962, 4,378,015 have retractable needles which are hidden until activation. Upon activation, the needle extends from the bottom of the device and penetrates the user's skin to deliver medicament. As none of these devices involves delivery of the medicament using jet injection, the medicament delivery location is limited by the length of the needle. For example, if delivery in the subcutaneous region is desired, the needle must be long enough to reach the subcutaneous region. Furthermore, as auto-injectors operate like syringes, the injection time is several seconds or longer. In contrast, jet injectors typically inject in fractions of a second.

Thus, there exists a need for a jet injector with a short needle to reduce the pressure at which the jet injector must eject the medicament for proper delivery.

SUMMARY OF THE INVENTION

The present invention relates to a needle assisted jet injector. In one embodiment, the injection device includes a housing; a nozzle assembly defining a fluid chamber, having an opening for slidingly receiving at least a portion of the needle and removably associated with the housing; a plunger movable in the fluid chamber; a trigger assembly; an energy generating source operatively associated with the trigger assembly so that movement of the trigger assembly activates the energy source to move the plunger in a first direction to expel a fluid from the fluid chamber; and a retractable injection-assisting needle at a distal end of the injector. The retractable injection-assisting needle has a needle tip located at a distal end of the needle with at least a portion configured and dimensioned to slide through the nozzle assembly opening; a discharge channel within the needle tip and terminating in an orifice through which the fluid is expelled; a body portion to direct fluid towards the discharge channel; a plunger receptor configured and dimensioned to receive at least a portion of the plunger; and a retraction element operatively associated with the nozzle assembly. The needle is located within the nozzle assembly in a retracted position prior to activation of the energy source. Movement of the plunger in the first direction upon activation of the energy source results in at least a portion of the needle tip extending beyond the nozzle assembly opening and the retraction element returns the needle tip to the retracted position after activation of the energy source.

The retraction element can be a resilient O-ring, a spring, or a flexible membrane which moves to allow extension of the needle tip beyond the nozzle assembly opening and then returns to its original position to return the needle tip to its retracted position. The needle body can have an exterior surface which includes a ridge or recess for accommodating the retraction element. A shoulder can be disposed between the needle tip and the needle body for accommodating the retraction element. Preferably, the needle tip has a length of approximately 1–5 mm.

In another embodiment, the injector has a non-retracting fixed needle. The injection-assisting needle comprises a body fixed to a distal end of the nozzle assembly and a discharge channel extending through the needle body, in fluid communication at a first end with the fluid chamber, and terminating at a second end in an orifice through which the fluid is expelled. Preferably, the body has a length of approximately 1–5 mm.

The present invention also relates to a method of delivering medicament to an injection site of a patient. The method includes the steps of: inserting a needle into a needle insertion point, said needle having a length less than 5 mm and being operatively associated with an orifice in a nozzle assembly in fluid communication with an ampule chamber containing the medicament; activating an energy mechanism; and coupling a pressure wall member disposed and movable within the ampule chamber to the activated energy mechanism to move the pressure wall member at a speed sufficient to eject the medicament from the ampule chamber through the orifice and needle under a pressure which is sufficient to deliver a substantial portion of the medicament to the injection site. The needle insertion point is located more superficial than the injection site.

The method preferably includes the steps extending a needle from a shield prior to inserting the needle into the needle insertion point and then retracting the needle into the shield after the medicament has been delivered to the injection site.

DESCRIPTION OF THE PREFERRED EMBODIMENTS

Figure 1:
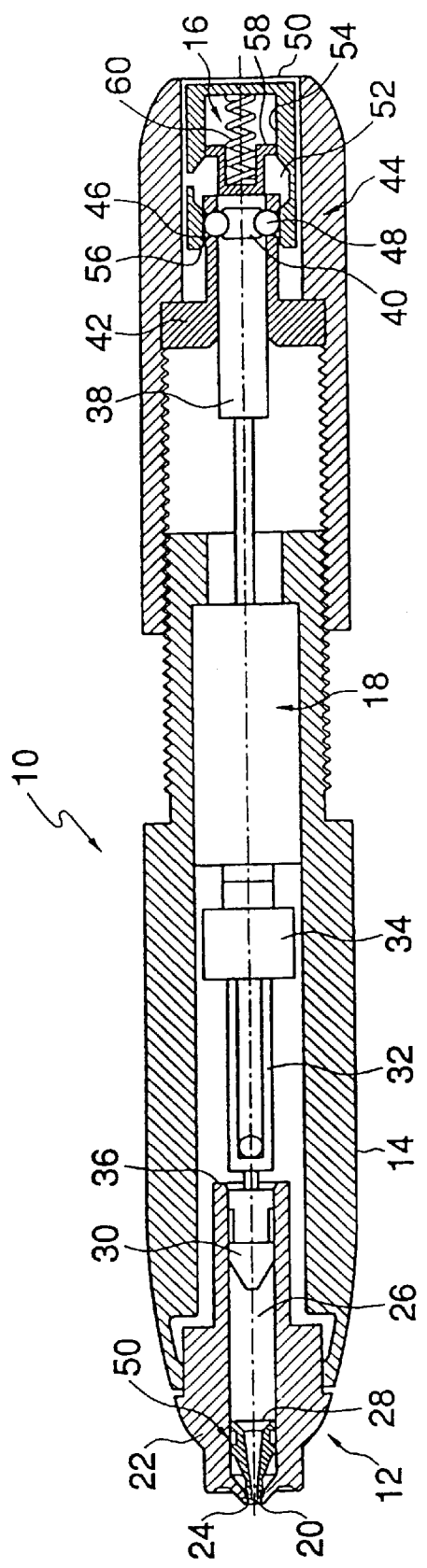
FIG. 1 is a cross-sectional view of a needle assisted jet injector according to the present invention.

For convenience, the same or equivalent elements of the invention of embodiments illustrated in the drawings have been identified with the same reference numerals. Further, in the description that follows, any reference to either orientation or direction is intended primarily for the convenience of description and is not intended in any way to limit the scope of the present invention thereto.

As shown in FIG. 1, a jet injector 10 according to the present invention comprises a nozzle assembly 12 attached to a housing 14. As used in this application, the term distal shall designate the end or direction toward the front of jet injector 10. The term proximal shall designate the end or direction toward the rear of the injector. The term longitudinal designates an axis connecting nozzle assembly 12 to jet injector 10, and the term transverse designates a direction substantially perpendicular to the longitudinal direction including arcs along the surface of jet injector 10, or nozzle assembly 12.

Nozzle assembly 12 can be threadably connected to housing 14 such that it can be readily attached and detached. Alternatively, other known structures for mounting or attaching two components can be utilized as well to detachably mate nozzle assembly 12 to housing 14. In this manner, injector 10 can be reused with various nozzle assemblies that may contain different medications of different doses either together or at different times. For instance, nozzle assembly 12 can be prefilled with medication and disposed of after each use. Further, a medication filling device such as a coupling device can be used to fill the fluid chamber with medication. U.S. Pat. No. 5,769,138 to Sadowski et al., the disclosure of which is herein incorporated by reference, is directed to such a coupling device.

A trigger assembly 16 is located at the proximal end of housing 14. Trigger assembly 16 activates and triggers an energy source or energy generating means 18 which forces medicament out of nozzle assembly 12. Energy source 18 can be a coil spring, a gas spring, or a gas propellant.

According to a first embodiment of the present invention, nozzle assembly 12 has an injection assisting needle 20 movable within nozzle assembly 12. Needle 20 will be discussed in detail after first describing the other components of injector 10. The nozzle assembly 12 includes a nozzle member 22 having an opening 24 at the distal end, preferably having a diameter of about 0.04–0.4 inches or any other suitable diameter that would allow for the introduction of injection assisting needle 20 therein. Nozzle member 22 includes a cylindrical fluid chamber 26 terminating at the distal end in a right circular cone 28. Cone 28 can be a convex cone (as shown), a right circular cone, or any other suitable configuration. A plunger 30 having a pressure wall contoured to cone 28 is positioned to slide within fluid chamber 26. Plunger 30 can include sealing means such as one or more O-rings or the like (not shown) that are formed around its outer periphery to provide a seal, or the plunger itself can be a seal, as described in U.S. Pat. No. 5,062,830, the disclosure of which is incorporated herein by reference. The plunger can also include additional sealing means at spaced intervals to provide a better seal.

Plunger 30 is connected to a ram 32 which in turn is connected to energy source 18. Alternatively, ram 32 can be integrally formed with an energy mechanism if desired. An inertia mass 34 is connected to or integrally formed with ram 32 near the end of ram 32 closest to plunger 30. Inertia mass 34 can be removably connected to ram 32 such that the mass can be adjusted to accommodate different types of injections, taking into consideration, for instance, the viscosity of the medication, the initial pressure build up desired, the strength of energy source 18, and the depth of injection penetration, etc. Inertia mass 34 cooperates with ram retainer 36 to limit the distance that ram 32 can travel toward nozzle assembly 12. One important safety aspect of this feature is that ram 32 cannot become a dangerous projectile if injector 10 is fired when nozzle assembly 12 is not present.

Trigger assembly 16 includes a trigger extension 38 having a trigger engaging notch 40. Trigger extension 38 is attached to the end of ram 32, for example, by a threaded engagement. Trigger assembly 16 also comprises a latch housing sleeve 42 fixedly attached to an actuating mechanism 44. Actuating mechanism 44 is shown as a threaded coupling that operates by rotation movement. Alternatively, the actuating mechanism of the provisional application of DeBoer et al. Ser. No. 60/094,163 filed Jul. 27, 1998 and entitled "Loading Mechanism for Medical Injector Assembly", the disclosure of which is herein incorporated by reference, can be used. Latch housing sleeve 42 has a throughbore dimensioned to allow passage of trigger extension 38. Latch housing sleeve 42 further has a plurality of sidewall openings 46 dimensioned to allow passage of balls or ball bearings 48. A tubular button 50 having one open end and a closed end is telescopingly positioned with latch housing sleeve 42 as shown. Button 50 has a circumferential or annular groove 52 formed on an inner wall 54 thereof to allow portions of the balls 48 to engage groove 52 when trigger assembly 16 is in the fired position, i.e., not engaged with trigger extension 38 (not shown). Balls 48 are positioned so that they are substantially flush with an inner side wall surface 56 of latch housing sleeve 42 to allow trigger extension 38 to pass through latch housing sleeve 42. A latch ball retaining cup 58 is telescopingly positioned within button 50. A compression spring 60 is positioned between the cup 58 and button 50 to bias button 50 and cup 58 away from each other in the axial direction.

Figure 2:
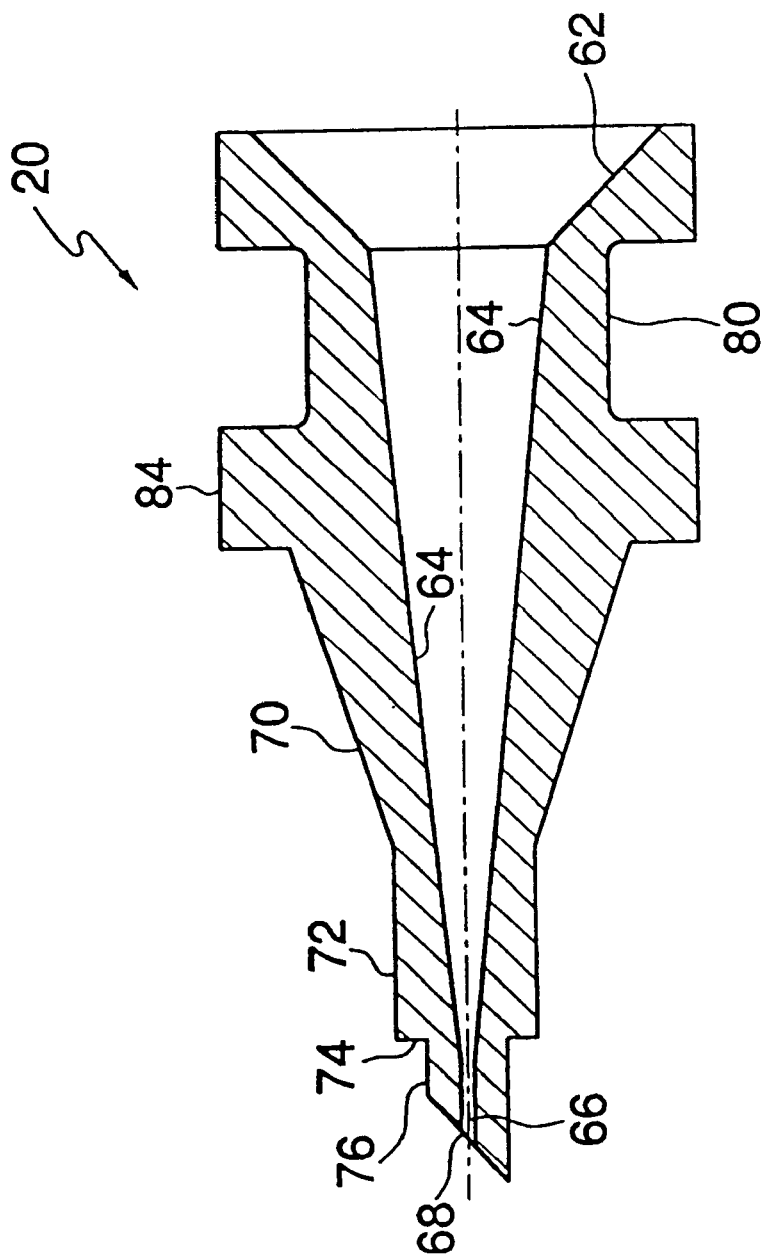
FIG. 2 is a cross-sectional view of the needle on the jet injector of FIG. 1.
Figure 3:
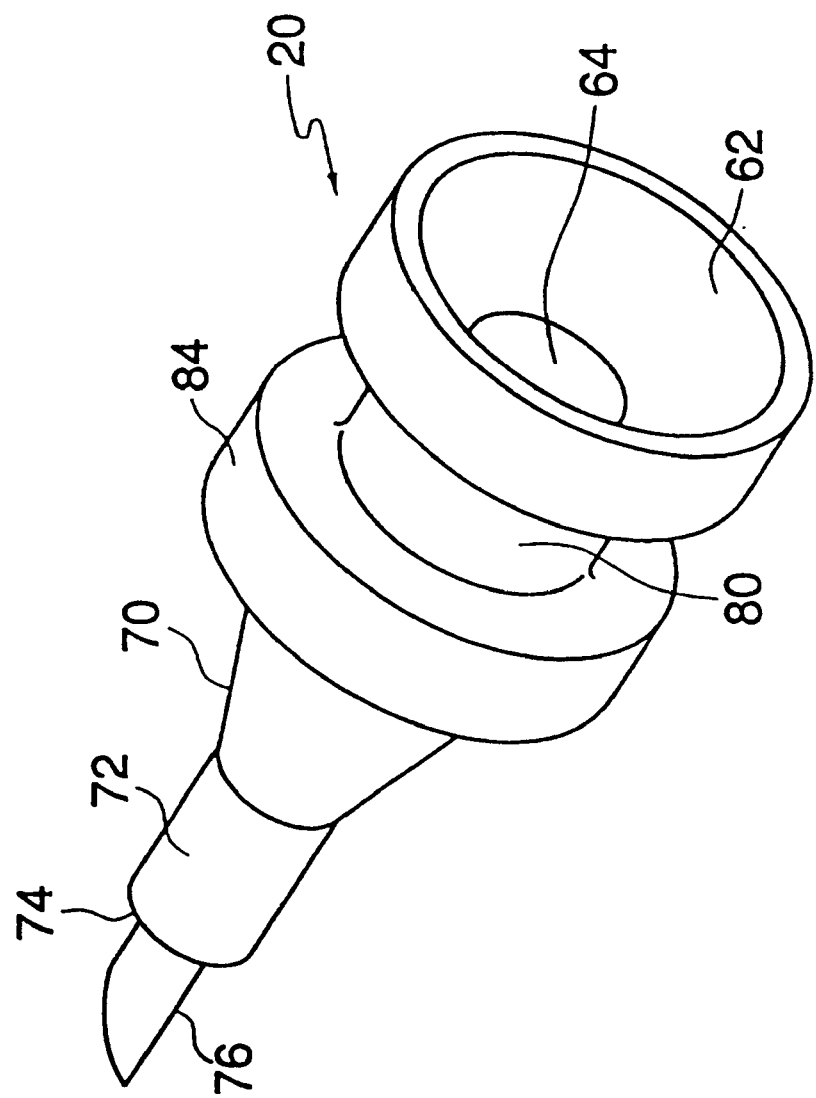
FIG. 3 is a perspective view of the needle of FIG. 2.

The structure of injection assisting needle 20 is best seen in FIGS. 2 and 3. Needle 20 has a plunger receptor 62 at the proximal end which is configured to accommodate plunger 30 as it slides within fluid chamber 26. Although plunger receptor 62 can be of any shape conforming to the exterior profile of plunger 30, it is preferably conical. A needle inner wall 64 is contoured to narrow like a funnel to a needle discharge channel 66 to accelerate the fluid as it is discharged. Needle discharge channel 66 extends to a discharge orifice 68 at the distal end of needle 20. Needle discharge orifice 68 has a diameter of 0.004 to 0.012 inches. Preferably, the diameter is 0.005 to 0.0075 inches.

The outer periphery of needle 20 can be of varied geometries such that it fits within fluid chamber 26 of nozzle assembly 12. Advantageously, needle 20 has a conical body section 70 which narrows gradually or tapers towards a cylindrical body section 72 of smaller circumference. Preferably, a shoulder 74 is positioned to separate a needle tip 76 from cylindrical body section 72. Needle tip 76 is also cylindrical, but has a smaller circumference than cylindrical body section 72 such that needle tip 76 can fit within and extend through opening 24 of nozzle assembly 12. However, cylindrical body section 72 of needle 20 has a circumference such that shoulder section 74, existing at the transition between cylindrical body section 72 and needle tip 76, prevents cylindrical body section 72 from existing within opening 24. The length of needle tip 76 from its end to shoulder 74 is approximately 1 to 5 mm. Thus, needle tip 76 will penetrate the skin to a depth less than 5 mm. It should also be noted that although needle tip 76 is shown having a single beveled end at a 45° angle, needle tip 76 can have any shape that penetrates the skin.

Figure 4:
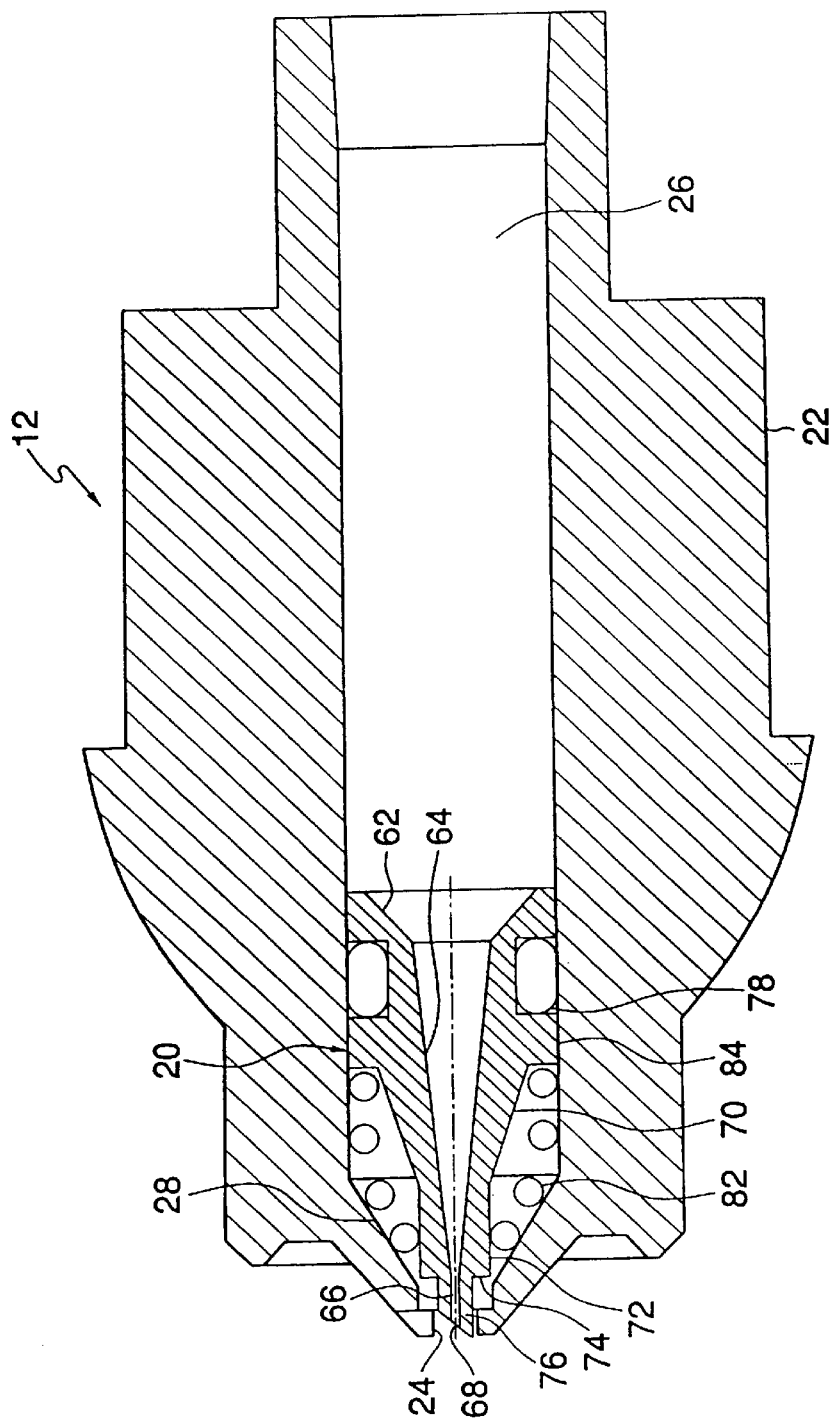
FIG. 4 is an enlarged cross-sectional view of the jet injector of FIG. 1 with the needle in the retracted position.
Figure 5:
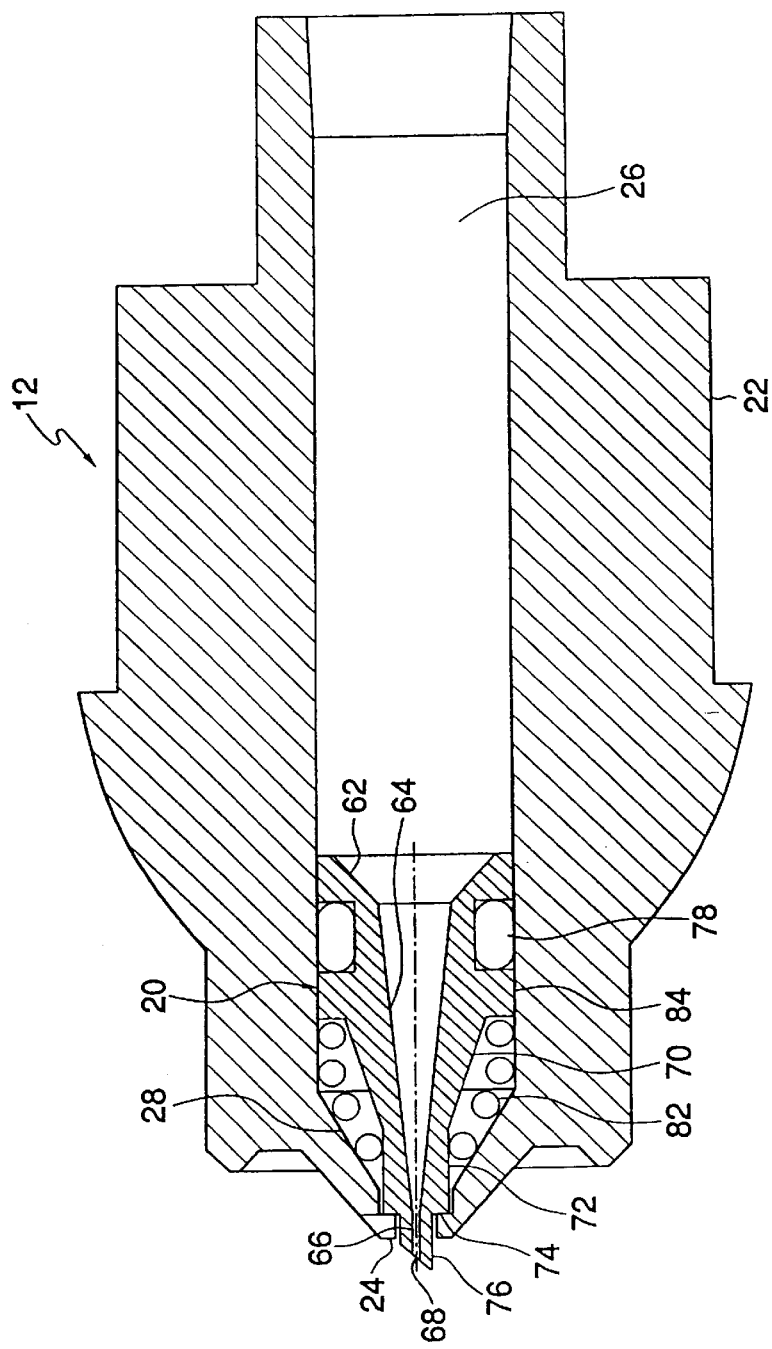
FIG. 5 is an enlarged cross-sectional view of the jet injector of FIG. 1 with the needle in the extended position.

As shown in FIGS. 4 and 5, needle 20 is positioned coaxially and retractably within the distal end of fluid chamber 26 such that when injector 10 is fired, needle tip 76 extends out opening 24 of nozzle assembly 12 at a speed sufficient to penetrate the outer layer of skin. By inserting needle tip 76 to a depth less than 5 mm, only the epidermis of the skin is penetrated and the pressure needed to deliver the medicament to the desired region by jet injection is lower than that would otherwise be needed. While syringes and auto-injectors delivery the medicament to the depth of the needle, the needle assisted jet injector according to the present invention delivers the medicament to a depth deeper than the length of the needle. This depth can include any region of the skin and beyond including intradermal, subcutaneous, and intramuscular.

To provide a seal between needle 20 and fluid chamber 26, needle 20 includes a sealing means such as an O-ring(s) 78 or the like formed around the outer periphery of needle 20 and accommodated by slot 80. In an alternative embodiment shown in FIG. 6, needle 120 itself is the seal. Thus, slot 80 is not needed. Needle 120 also differs from needle 20 in that cylindrical body section 72 is absent so that conical body section 70 terminates at shoulder 74.

FIG. 5 illustrates injection assisting needle 20 in its extended position. Needle tip 76 extends beyond the distal end of nozzle assembly 12. Shoulder 74 abuts the bored out inner section of nozzle opening 24 to prevent needle 20 from extending beyond needle tip 76. A retraction element 82, in this embodiment a spring, is compressed to provide a recoil force once the medicament is expelled so that needle tip 76 will retract back into nozzle opening 24. Needle 20 preferably has a ridge 84, the distal surface of which provides an annular area for the compression of retraction element 82. Alternatively, a washer can be used instead of the ridge 84 to contain O-ring 78 and compress the retracting mechanism during operation.

Figure 6:
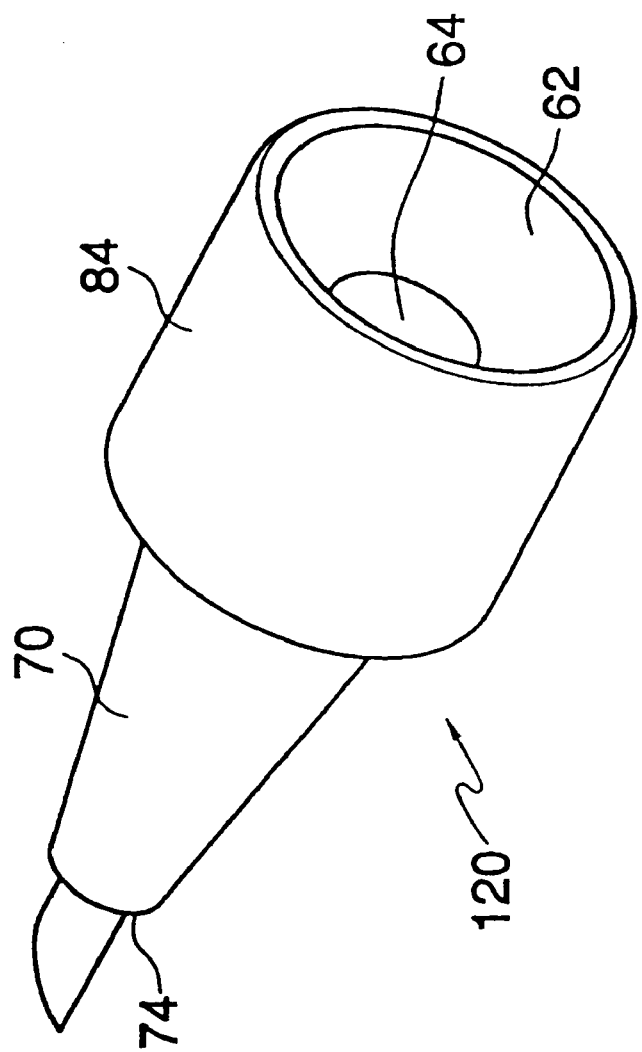
FIG. 6 is a perspective view of a second embodiment of the needle according to the present invention.
Figure 7:
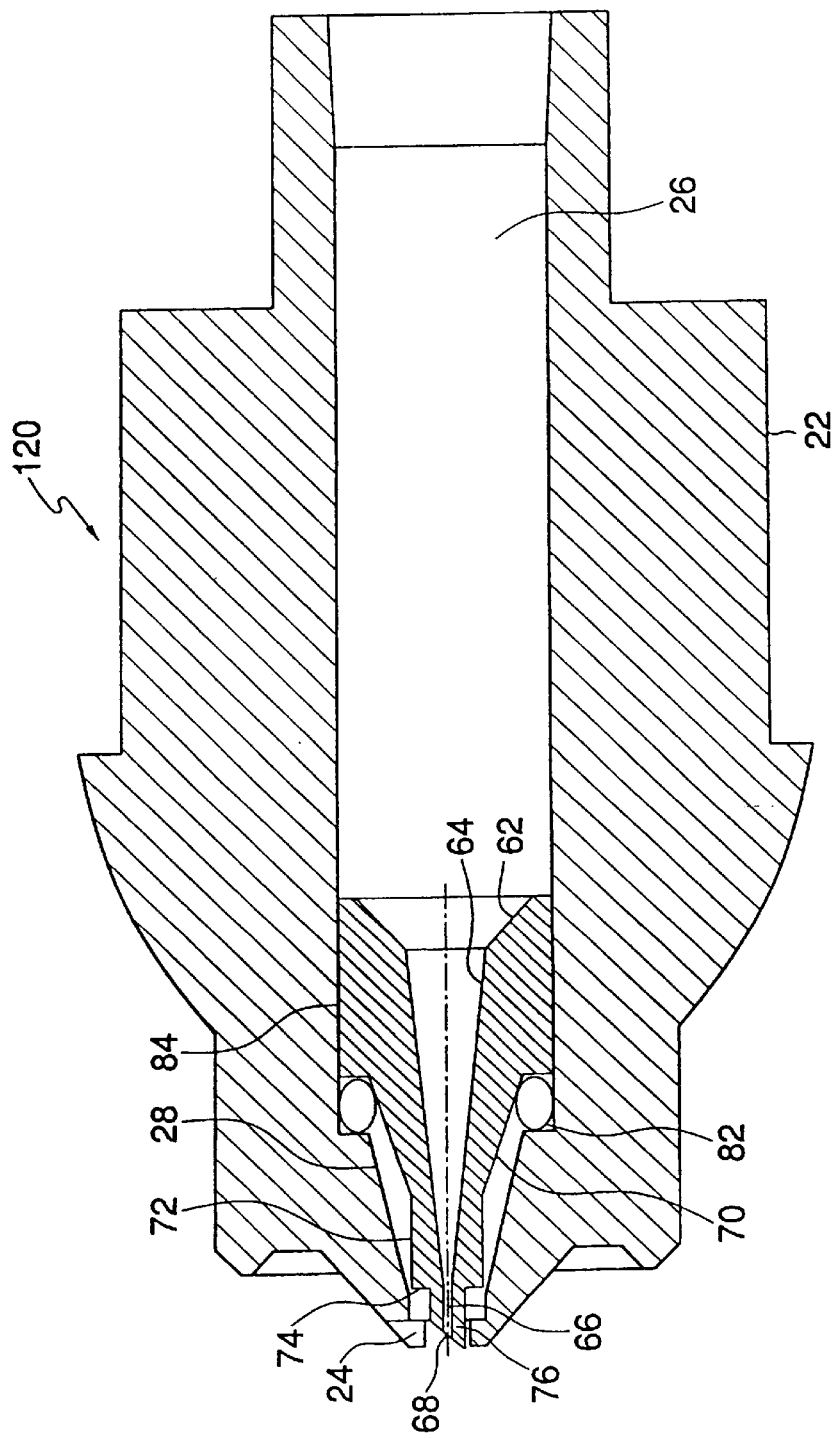
FIG. 7 is a partial cross-sectional view of a jet injector according to the present invention with the needle of FIG. 6 in the retracted position.
Figure 8:
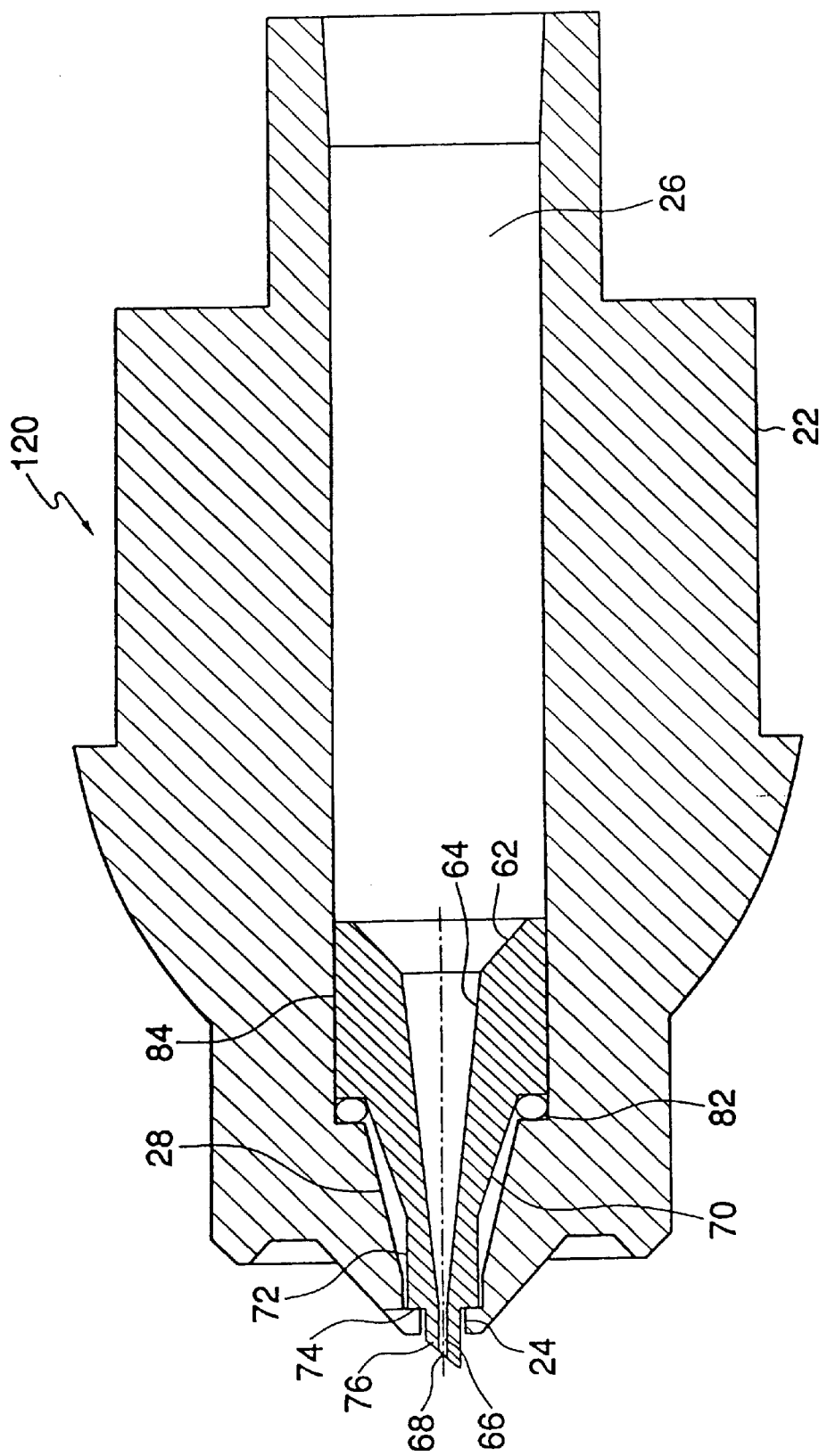
FIG. 8 is a partial cross-sectional view of a jet injector according to the present invention with the needle of FIG. 6 in the extended position.

FIGS. 7 and 8 show needle 120 of FIG. 6 with nozzle assembly 12 in which retraction element 82 is a resilient O-ring or other like material known to those skilled in the art. When an O-ring is used as retraction element 82, it can also act as a sealing mechanism, and for this reason the O-ring is preferred. The interior of needle 120 is similar to that of needle 20. FIG. 7 illustrates needle 120 in the retracted condition, before expelling medicament, and FIG. 8 shows the extended condition during which medicament is expelled. Similar to embodiments previously described, this embodiment functions to extend the needle tip 76 beyond nozzle opening 24 and penetrate the outer layer of the patient's skin during operation. Also, similar to embodiments previously described, needle 120 also preferably has ridge 84 around the proximal end to provide a surface which compresses the resilient material when the injector is triggered.

Figure 9:
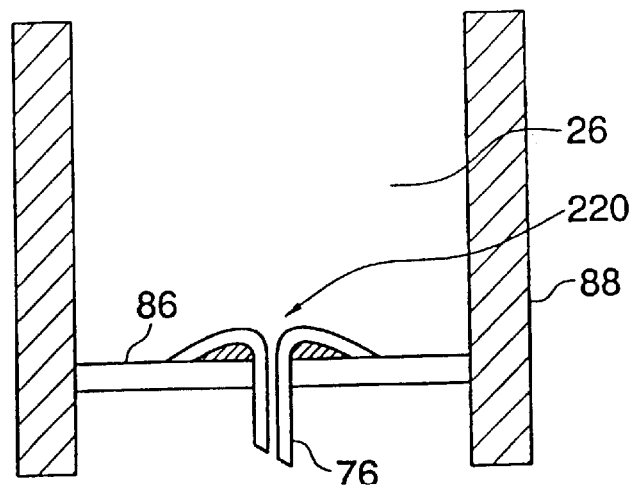
FIG. 9 is a cross-sectional view of another embodiment of the present invention with a flexible member as the retraction element and the needle in the retracted position.
Figure 10:
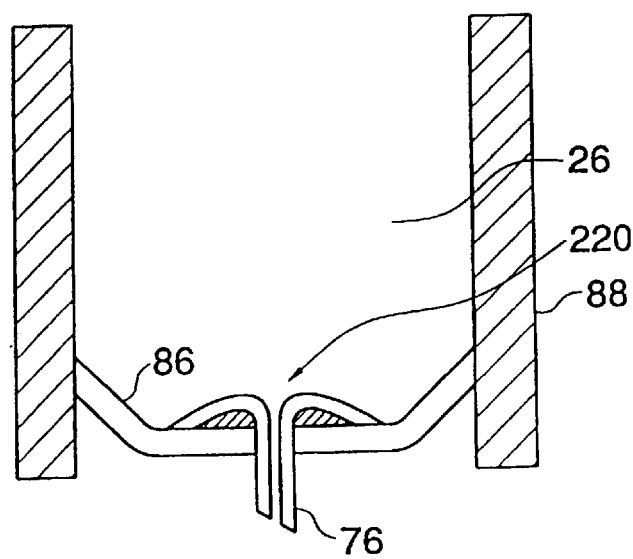
FIG. 10 is a cross-sectional view of the embodiment of FIG. 9 with the needle in the extended position.

Another embodiment of the present invention, shown in FIGS. 9 and 10, uses a flexible member 86 as the retraction element. FIG. 9 illustrates the neutral condition before expelling the medicament. Flexible membrane 86 spans between walls 88 of nozzle assembly 12 which define fluid chamber 26 for holding medicament. Similar to embodiments previously described, the distal end of nozzle walls 88 act to conceal needle tip 76 until the injector is fired. Needle 220 is attached to flexible membrane 86 by any conventional means known to those skilled in the art. Preferably, needle 220 is integrally attached to flexible membrane 86 with an adhesive. FIG. 10 shows needle 220 in its extended position where the needle tip 76 extends beyond the end of walls 88 such that needle tip 76 penetrates the outer layer of skin to allow injection and deliver the medicine at reduced pressure.

Other embodiments of the present invention relate to injectors with a fixed needle, i.e. a non-retracting needle that permanently extends beyond the nozzle assembly. Both a one-piece and a two-piece nozzle assembly with a fixed needle can be used and are contemplated by this invention.

Figure 11:
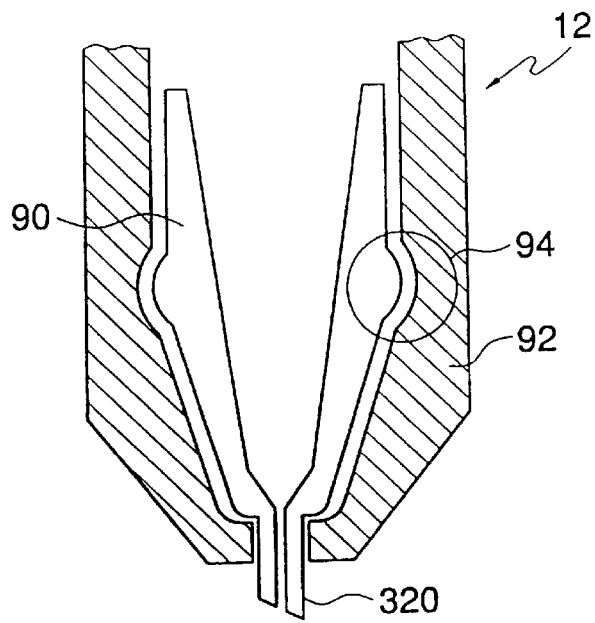
FIG. 11 is a cross-sectional view of a two piece nozzle assembly having a fixed needle.
Figure 12:
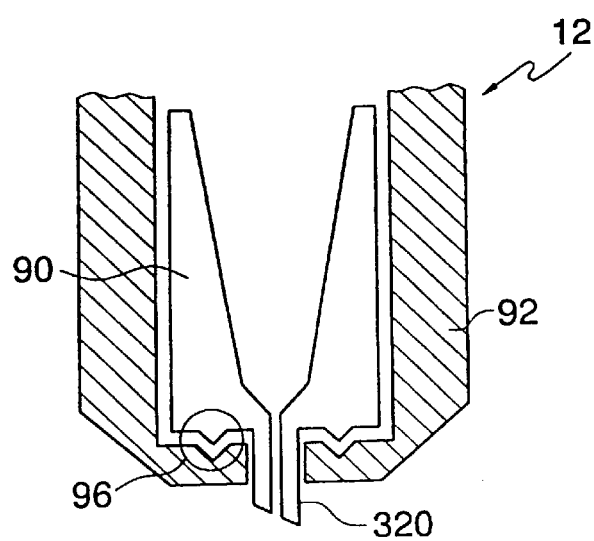
FIG. 12 is a cross-sectional view of another embodiment of a two piece nozzle assembly having a fixed needle.

FIGS. 11 and 12 show embodiments of the present invention with a two piece nozzle assembly with a fixed needle 320. A first section 90 of nozzle assembly 12 has needle 320 at the distal end and can either be attached internally or externally to a second section 92 to form nozzle assembly member 12. Although any conventional attaching means can be used, such as solvent or adhesive bonding, FIG. 11 shows a preferable friction-fitting or snapping attaching means 94 for both internal and external attachment of first section 90 and second section 92. FIG. 12 shows a preferable ultrasonic bonding means 96 of attachment. Although ultrasonic bonding features 96 can be placed at any location to attach the two pieces, preferably, the ultrasonic bonding features 96 are along the distal end at the interface between first and second sections 90, 92 to facilitate ease of manufacturing.

Figure 13:
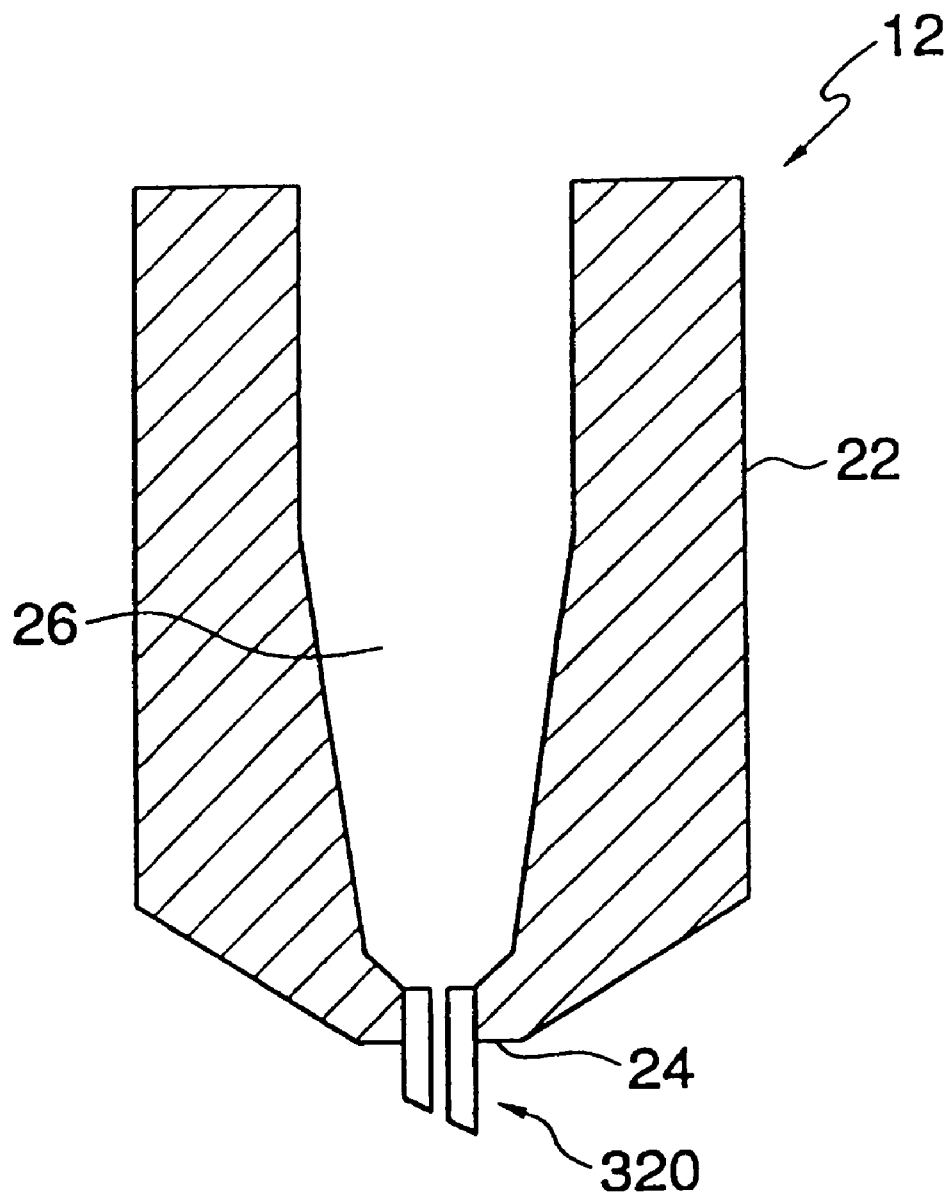
FIG. 13 is a cross-sectional view of another embodiment of a two piece nozzle assembly having a fixed needle.

Another embodiment of a multi-piece nozzle assembly with fixed needle 320 is shown in FIG. 13. The nozzle assembly consists of nozzle member 22 having an opening 24 designed to receive a tubular insert to create fixed needle 320. Although FIG. 13 shows a multi-piece nozzle assembly, fixed needle 320 can be made to be integral with nozzle assembly 12.

Figure 14:
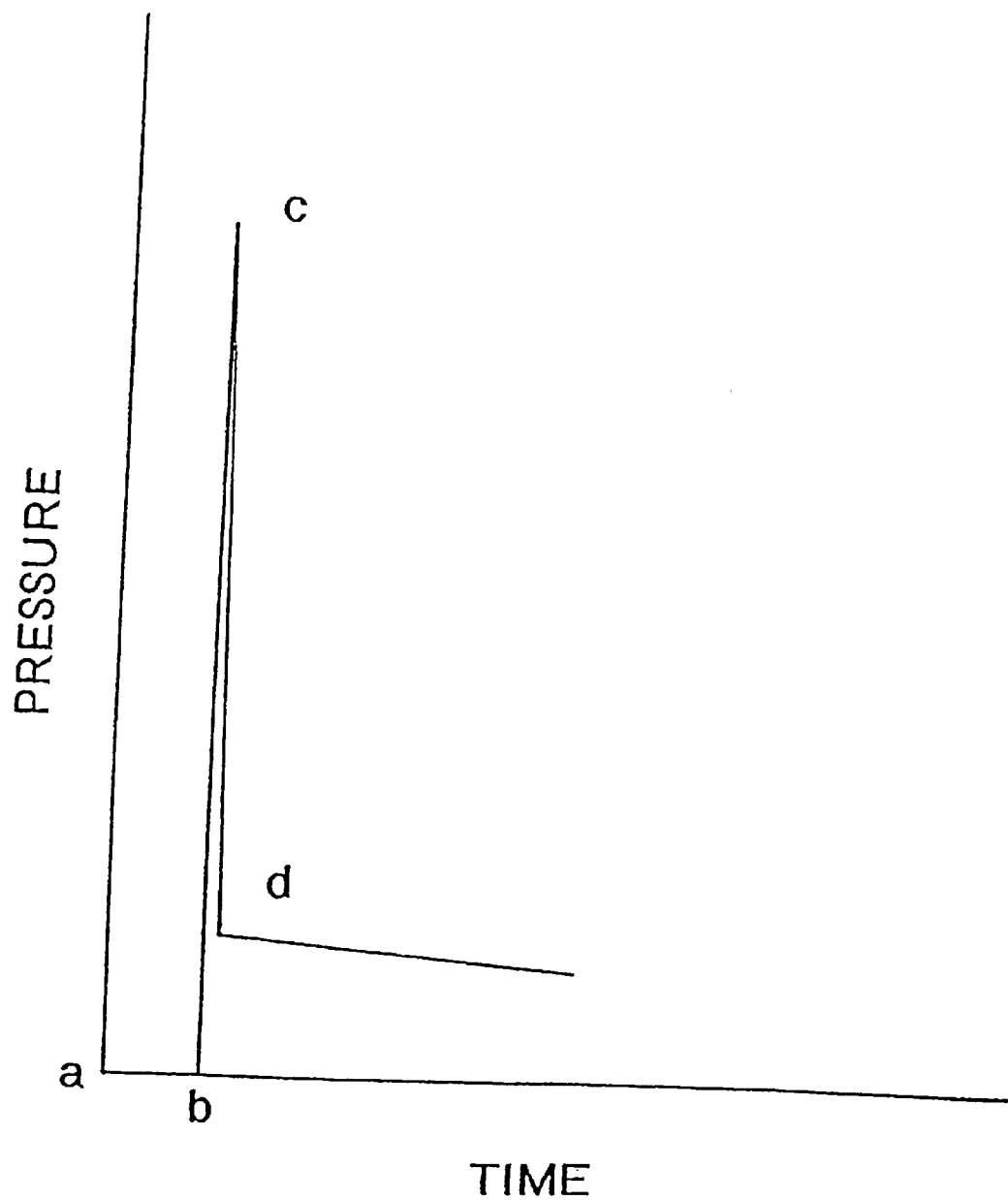
FIG. 14 is a schematic expressing a pressure-time curve for a jet injector.

A significant advantage of the needle assisted jet injector according to the present invention is that it allows for a lower pressure to deliver the medicament. In this regard, administering an injection using either a fixed or retractable needle requires less energy and force than conventional jet injector devices. FIG. 14 shows a pressure-time curve for a jet injector. The peak pressure at point c is the pressure needed to penetrate the skin and point d and beyond is the pressure at which a jet stream of medicament is delivered. Needle assisted jet injectors do not need to achieve as high as peak pressure as conventional jet injectors because the outer layer of skin is penetrated by the needle. Therefore, a lower peak pressure can be used to deliver the medicament to the desired region. It is also possible that a lower steady state pressure can be used to deliver the jet stream after the needle and the jet injection have reached the desired region.

Experimentation has confirmed that the needle assisted injector according to the present invention can be operated using a lower generating energy source and still maintain the quality of the injection. Specifically, experimentation has shown that a higher percentage of successful injections can be achieved with a needle assisted jet injector having a needle that penetrates the skin to a depth of 1 mm and 20 lb. energy generating means as with conventional needleless jet injectors having 55 lb. energy generating means. Similar results have been achieved with needles that penetrate 1–3 mm and energy generating sources providing 20 lbs. and 40 lbs. of force.

Another advantage of the needle assisted jet injector according to the present invention is the decreased injection time compared to syringes or auto-injectors. As previously discussed, auto-injectors and syringes have injection times of several seconds or more. During this injection time, the quality of the injection can be compromised due to any number of factors. For example, the patient could move the syringe or auto-injector prior to completion of the injection. Such movement could occur either accidently or intentionally because of injection-related pain. In contrast, the needle assisted jet injector, like other jet injectors, has an injection time around 0.25 seconds. The short injection time minimizes the possibility of compromising the quality of the injection.

While it is apparent that the illustrative embodiments of the invention herein disclosed fulfil the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

What is claimed is:

1. A jet injection device comprising a housing, a retractable injection-assisting needle at a distal end of the injector, a nozzle assembly defining a fluid chamber, having an opening for slidingly receiving at least a portion of the needle and being removably associated with the housing, a plunger movable in the fluid chamber, a trigger assembly, and an energy generating source operatively associated with the trigger assembly so that movement of the trigger assembly activates the energy source to move the plunger in a first direction to expel a fluid from the fluid chamber, said retractable injection-assisting needle comprising:

a needle tip located at a distal end of the needle with at least a portion configured and dimensioned to slide through the nozzle assembly opening;

a discharge channel within the needle tip and terminating in an orifice through which the fluid is expelled;

a body portion to direct fluid towards the discharge channel;

a plunger receptor configured and dimensioned to receive at least a portion of the plunger; and a retraction element operatively associated with the needle and disposed substantially within the nozzle assembly;

wherein the needle is located within the nozzle assembly in a retracted position prior to activation of the energy source; movement of the plunger in the first direction upon activation of the energy source results in (1) at least a portion of the needle tip extending beyond the nozzle assembly opening to a needle insertion point, and (2) the fluid is expelled through the needle tip and past the needle insertion point to an injection site, the retraction element returns the needle tip to the retracted position after activation of the energy source, the needle insertion point is located at the needle tip and less than about 5 mm from the nozzle assembly opening, and the injection site is substantially remote from the needle tip.

2. The injection device of claim 1, wherein the retraction element is a resilient O-ring, a spring, or a flexible membrane which moves to allow extension of the needle tip beyond the nozzle assembly opening and then returns to its original position to return the needle tip to its retracted position.

3. The injection device of claim 1, wherein the needle body has an exterior surface which includes a ridge or recess for accommodating the retraction element.

4. The injection device of claim 1, wherein a shoulder is disposed between the needle tip and the needle body for accommodating the retraction element.

5. A jet injection device comprising a housing, a retractable injection-assisting needle at a distal end of the injector, a nozzle assembly defining a fluid chamber, having an opening for slidingly receiving at least a portion of the needle and being removably associated with the housing, a plunger movable in the fluid chamber, a trigger assembly, and an energy generating source operatively associated with the trigger assembly so that movement of the trigger assembly activates the energy source to move the plunger in a first direction to expel a fluid from the fluid chamber, said retractable injection-assisting needle comprising:

a needle tip located at a distal end of the needle with at least a portion configured and dimensioned to slide through the nozzle assembly opening;

a discharge channel within the needle tip and terminating in an orifice through which the fluid is expelled;

a body portion to direct fluid towards the discharge channel;

a plunger receptor configured and dimensioned to receive at least a portion of the plunger; and a retraction element operatively associated with the needle and disposed substantially within the nozzle assembly;

wherein the needle is located within the nozzle assembly in a retracted position prior to activation of the energy source; movement of the plunger in the first direction upon activation of the energy source results in at least a portion of the needle tip extending beyond the nozzle assembly opening and less than about 5 mm from the opening, the retraction element returns the needle tip to the retracted position after activation of the energy source, and the needle body has a funnel-shaped interior tapering towards the discharge channel to accelerate the fluid as it is discharged to a site that is substantially remote from the needle tip.

6. A method of delivering a medicament, comprising:

puncturing the epidermis with a needle tip to create a hole of less than about 3 millimeters in depth and confined to the epidermis; and jet injecting a medicament in a single injection at a pressure of less than about 4000 p.s.i. through the needle tip and hole to a layer of tissue below the epidermis and substantially remote from the needle tip, whereby the medicament is delivered in less than one second, and wherein the needle tip is part of a retractable needle of a jet injection device.

* * * * *

UNITED STATES PATENT AND TRADEMARK OFFICE
CERTIFICATE OF CORRECTION

PATENT NO.   : 6,428,528 B2
DATED        : August 6, 2002
INVENTOR(S)  : Sadowski et al.

It is certified that error appears in the above-identified patent and that said Letters Patent is hereby corrected as shown below:

<u>Title page,</u>
Item [75], Inventors, correct the spelling of "David M. DcBoer" to -- David M. DeBoer --

Signed and Sealed this

Tenth Day of December, 2002

JAMES E. ROGAN
*Director of the United States Patent and Trademark Office*